United States Patent [19]

Berger et al.

[11] Patent Number: 4,891,313
[45] Date of Patent: Jan. 2, 1990

[54] METHOD FOR DETERMINATION OF A COMPONENT OF A SAMPLE

[75] Inventors: Johann Berger; Fern DeLaCroix; Harvey Buck; Juergen Schrenk, all of Indianapolis, Ind.

[73] Assignee: Boehringer Manheim Corporation, Indianapolis, Ind.

[21] Appl. No.: 146,574

[22] Filed: Jan. 21, 1988

[51] Int. Cl.$^4$ ............................................. G01N 33/53
[52] U.S. Cl. ........................................ 436/7; 436/518; 436/536; 436/540; 436/512
[58] Field of Search .................... 435/7; 436/540, 512, 436/518, 536

[56] References Cited

U.S. PATENT DOCUMENTS

| | | | |
|---|---|---|---|
| 4,343,896 | 8/1982 | Wolters et al. | 436/540 |
| 4,433,059 | 2/1984 | Chang et al. | 436/540 |
| 4,469,787 | 9/1984 | Woods et al. | 435/512 |
| 4,469,796 | 9/1984 | Axen et al. | 436/518 |
| 4,624,930 | 11/1985 | Tanswell et al. | 436/500 |
| 4,659,678 | 4/1987 | Forrest et al. | 436/512 |
| 4,732,848 | 3/1988 | Lenz | 435/512 |
| 4,788,138 | 11/1988 | Tung | 435/7 |

*Primary Examiner*—Sam Rosen
*Attorney, Agent, or Firm*—Felfe & Lynch

[57] ABSTRACT

This invention relates to apparatus useful in determining a component or components of a test sample, as well as methods using these apparatus. Of particular interest are apparatus and methods which involve formation and determination of quarternary complexes.

11 Claims, 3 Drawing Sheets

One And One Half-wick Strip

Double-wick Strip

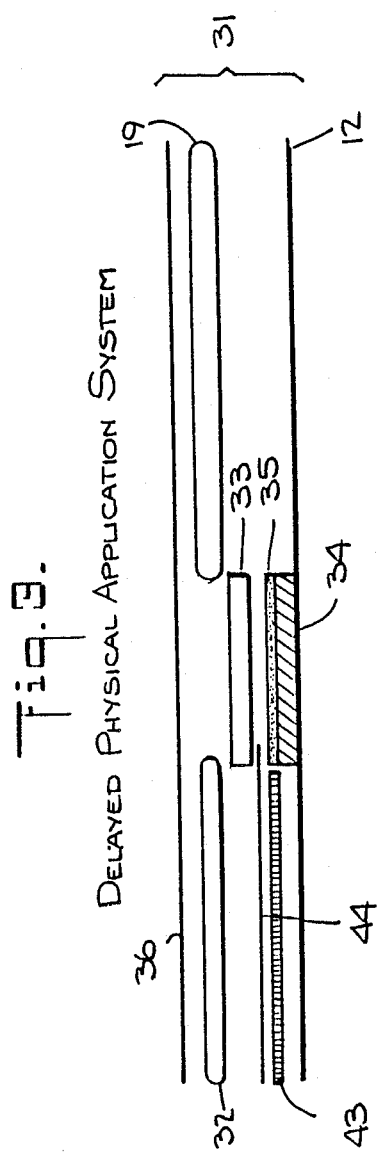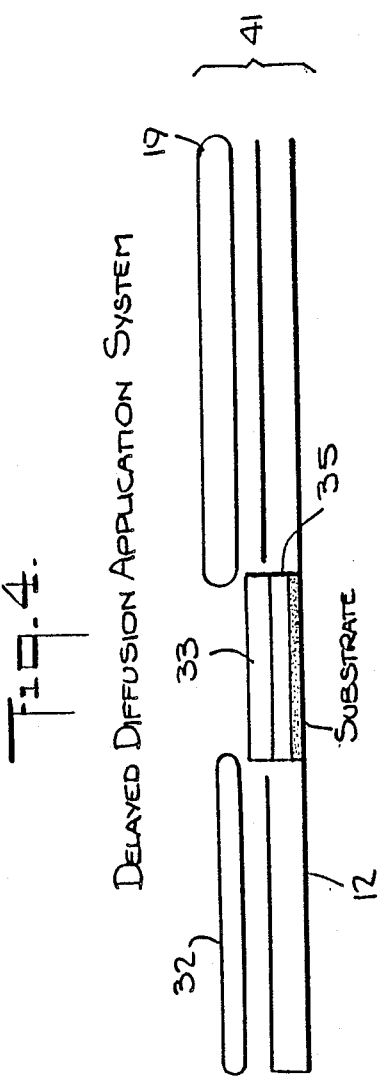

METHOD FOR DETERMINATION OF A COMPONENT OF A SAMPLE

FIELD OF THE INVENTION

This invention relates to an apparatus useful in determining an analyte in a fluid sample. It also relates to a method for determining an analyte in a sample, using a four member, or "quaternary" complex involving the analyte, a whole monoclonal antibody which binds to said analyte, a labeled monoclonal antibody Fab fragment which also binds to the analyte, where both of these are obtained from the same animal species, and a solid phase bound antibody which may or may not be monoclonal, which binds to the Fc portion of a monoclonal antibody but not to its Fab portion.

BACKGROUND AND PRIOR ART

The formation of sandwiches of antigen and antibody and their use in immunoassays has been in use for over fifteen years. The art has seen two distinct trends in the field. The earliest trend was toward the formation of ternary complexes, i.e., complexes of the form—$Ab_1$—$Ag$—$Ab_2^*$, where $Ab_2^*$ carries some label. The later trend is to multiple component systems, usually quaternary, but sometimes involving five or more components. The prior art discussion maintain this distinction.

I. Ternary Complex Formation

The patent literature contains many examples of inventions in this area. An early example of such an assay may be found in Schuurs, et al., U.S. Pat. No. 3,654,090 (1972), which is useful not only as historical background, but for an understanding of some of the key facets of this field.

Schuurs, et al. teaches detection of an antigen using a solid phase bound antibody against one epitope, or binding site, of the antigen, as well as a soluble, enzyme labeled antibody which binds with a second portion of the antigen. The method disclosed in Schuurs, et al. involves determination of the enzyme label after the sandwich between bound antibody, antigen, and labeled antibody forms. This is accomplished either in the solid phase, or in the liquid phase, by addition of a substrate for the enzyme label. Usually, the enzyme-substrate reaction produces a color or change in color, which can be recognized in "yes-no" tests, or quantitated where the amount of substance present is to be determined.

Absent from Schuurs, et al. is any discussion of monoclonal antibodies or antibody fragments and this is not surprising since Schuurs, et al. was filed in 1968, and issued in 1972, i.e., much earlier than the breakthroughs in hybridoma technology which occurred following the development of the Köhler-Milstein method for producing monoclonal antibodies.

Schuurs, et al. received another patent in 1974, U.S. Pat. No. 3,791,932, again directed to sandwich assays. This patent describes a so-called "forward" sandwich immunoassay. This type of assay calls for a specific order of steps, i.e., the sample being tested is first contacted with the insoluble binding partner and the reaction between these two is allowed to proceed to completion. The solid phase complexes are removed from the solution, and the second binding partner, containing an enzyme label, is then added to the solid phase. Following binding to the complex, the enzyme level is determined, following the standard techniques referred to, supra. Again, there is no mention of monoclonal antibodies or antibody fragments.

Ling, in U.S. Pat. No. 3,867,517 (1975), taught that enzymes were not the only label which could be used in sandwich assays. This patent describes a forward sandwich assaying as the label a radioactive antibody. The radioactive label was $^{125}I$, a standard radioisotope. Radiolabelling of antibodies is a standard technique, but assumes the presence of the proper amino acids in the antibody molecule for binding of the radioactive iodine. Otherwise, the label does not hold.

Schuurs, et al., received yet another patent in 1977, U.S. Pat. No. 4,016,043. This patent claims to teach a simpler version of rudimentary sandwich assays. It teaches using an insoluble component of an antigen-antibody reaction and a labeled sample of the same component. This method assumes that the antigen being detected has two identical epitopic sites. Further, the use of two identical receptors precludes the use of "simultaneous" assays, which are discussed infra. The consequences of this is that the Schuurs '043 assay can take as long as 60 hours to complete. In clinical or diagnostic laboratory, the large amount of time requires is unacceptable.

Piasio, et al., U.S. Pat. No. 4,098,876 (1978) taught a "reverse" sandwich assay. This patent is important because it showed, first, that the component being determined could be bound to the soluble, labeled antibody first, and the immobilized antibody second. It was also an improvement in that a washing step was eliminated, which meant that time was saved in performing the assay. Piasio, et al. teach that their assay could, ideally, be completed in under one-half hour. This paradigmatic system was not realized in their examples, but the time was substantially less than the 60 hours for Schuurs, et al., discussed supra. A significant drawback of the method is that it requires enormous amounts of immobilized antibody.

Niswender, U.S. Pat. No. 4,048,298 (1977), is actually not a sandwich assay, but shows an invention where an immobilized antibody was used to bind another antibody. This patent teaches an interesting variation on older competitive immunoassays. Niswender contacts a solid phase bound antibody with the sample being assayed as well as a second, radiolabeled antibody which binds to the first, but not to the component being determined. The effect of this is to allow the investigator to determine substance present by determining how much radiolabeled antibody binds to the solid phase.

This patent shows that antibodies can bind to other antibodies rather than just antigens. This property is important in more recent assays, some of which are discussed infra.

Schwarzberg, U.S. Pat. No. 4,235,689 (1980) recognized that antibodies possess two distinct portions, the Fc portion, or "constant" region, and the Fab portion, which is the part of the antibody which binds to an epitopic site. Schwarzberg prepared complexes of labeled Fab fragments bound to a ligand, such as a polypeptide. This complex is then used in so-called "competitive" assays. No solid phase binding, or sandwich assays, are described.

Jeong, et al., U.S. Pat. No. 4,244,940 (1981) teaches a "simultaneous" sandwich immunoassay. Such an assay requires an antigen with different epitopic sites, because two different antibodies or receptors must be used, for the reasons elaborated upon supra.

With Jeong, et al., it will be seen that by 1981 the state of the art in this field did teach forward, reverse, and simultaneous assay, always with ternary complexes (i.e., complexes of three species) being formed. The art had begun to see the use of Fab fragments as "linker" molecules (Schwarzberg), but they had not been used as an essential part of an immunoassay system, nor had monoclonal antibodies been used.

Both of these ideas were taught in patents which issued in 1983. David, et al., U.S. Pat. No. 4,376,110 (1983), overcame a prejudice in the art that monoclonal antibodies were not "sticky" enough, i.e., possessed insufficient affinity for use in sandwich assays. David, et al., taught that all three forms of ternary sandwich assays could be performed with monoclonal antibodies, as long as they both had affinities of at least $10^8$ liters/mole. Moussebois, et al., in U.S. Pat. No. 4,397,060 (1983), taught an agglutination assay could be performed using Fab fragments bound to a solid support. This patent shows, yet again, that Fab fragments were not being considered as partners of immunoassays, even though monoclonal antibodies themselves were now being used.

Gallati, et al., U.S. Pat. No. 4,467,031 (1984) taught a specific sandwich assay, for determination of carcinoembryonic antigen (CEA). The key feature of this invention was the use of different salt concentrations to improve complex formation. It is a "forward" sandwich assay, as the term is defined herein, and discusses the possibility of two monoclonal antibodies being used in the assay. It will be seen that this, too, is a ternary complex, and that an Fab fragment is not being used.

Woods, et al., U.S. Pat. No. 4,469,787 (1984) teaches a sandwich assay which requires the binding of a label to the Fc portion of a second antibody. The label is not directly attached to the second antibody, rather, Woods et al. assert invention in that the label is bound to the Fc portion of the antibody after the ternary complex is formed. This is done so as to prevent interference between the label and the immobilized first antibody.

U.S. Pat. No. 4,486,530 (1984), which issued to David, et al., and is a continuation in part of U.S. Pat. No. 4,376,110, discussed supra, again teaches ternary monoclonal antibody sandwiches and their detection. This patent adds to the art by showing that sandwich assays can be performed in homogeneous phase, i.e., without phase separation. This is performed by labeling the monoclonal antibody components of the ternary complexes with labels which do not react unless brought together by the "glue" of a multiepitopic antigen.

Carro, et al., U.S. Pat. No. 4,522,922 (1985) combine sandwich assays with an older form of immunoassay, the so-called "precipitation" test. This invention teaches formation of a ternary sandwich, followed by addition of a precipitating agent to precipitate the complex out of solution. This is a radioimmunoassay, which employs polyclonal antisera.

The most recent patents in the field show modifications on the basic sandwich principle. Petska, in U.S. Pat. No. 4,623,621 (1986), teaches that an oligomeric protein can be measured by using a solid phase bound monoclonal antibody which is specific for an epitope present once on the repeating protein portion of the molecule. After solid phase binding, a second sample of the same monoclonal antibody, only labeled, is bound. Again, a ternary complex is formed, only with whole antibodies, and simultaneous assaying is not possible.

II. Multiple Member Complex Formation

The earliest example of a quaternary system is exhibited by U.S. Pat. No. 4,343,896, which issued to Wolters, et al. This patent which is based on a disclosure filed in 1976, teaches the solid phase bound complex $Ab_1$—$Ab_2$—$Ag$—$Ab_3^*$. A crucial limitation in the Wolters patent is that $Ab_2$ and $Ab_3^*$ come from different animal species. The reason for this is because $Ab_1$ has to be directed against the constant region, i.e., "Fc" portion of $Ab_2$. All antibodies of a particular immunological class which come from the same animal species will have identical Fc portions. If $Ab_2$ and $Ab_3$ were from the same animal species, the art taught that not only would $Ab_1$—$Ab_2$—$Ag$—$Ab_3^*$ but one one would also obtain $Ab_1$—$Ab_3^*$, both of which would bind to the solid phase, causing interference and incorrect results.

Axen, et al., U.S. Pat. No. 4,469,796 (1984) teaches that more than three components may be involved in an immune reaction, but the only four part complex taught is a solid phase bound complex of $Ag$—$Ab_1$—$Ab_2$—$Ab_3^*$. It is noteworthy that in the description of reactants given at column 1, lines 41-60, Axen, et al. never mentions Fab fragments.

Tanswell, et al., U.S. Pat. No. 4,624,930 (1986) teaches four component complexes wherein a first and third receptor in solution bind to the antigen while a second solid phase antibody binds to the first antibody. Tanswell's teaching is generic to the use of a double antibody system and it does not specifically disclose monoclonal antibodies.

Forrest, et al., U.S. Pat. No. 4,659,678 (1987) goes beyond the four part binding discussed supra, and actually forms a pentavalent complex of antibody-hapten-antibody-antigen-antibody. The tail end of the complex is a radioactively labeled antibody. At least one antibody must be a monoclonal antibody.

Forrest, et al. detail at some length the advantages and disadvantages of multi-member complex forming assays. The solution to the problems set forth at, e.g., column 2, lines 1-5, is to use a solid phase bound mAb, to bind a complex of $Ab$—$Ag$—$Fab^*$. The only time a solid phase bound mAb is used to bind the complex $mAb_2$—$Ag$—$Fab^*$, however, Forrest requires that the $mAb_2$ be bound to another antigen, so that the solid phase complex $mAb_1$—$Ag_2$—$mAb_2$—$Ag_1$—$Fab^*$ is formed. It must be understood in this context, however, that "$Ag_2$" actually stands for a linking agent, as $mAb_2$ cannot possess two Ag binding sites.

SUMMARY OF THE INVENTION

This application is directed to a method for determining an analyte in a fluid sample, involving formation of a quarternary complex between a solid phase bound receptor which binds to a whole, unlabelled monoclonal antibody but not to a labelled Fab fragment or a labelled monoclonal antibody, a whole monoclonal antibody which binds to the analyte, the analyte itself, and a labeled Fab fragment of a monoclonal antibody. It is also directed to apparatus which can be used in such assays, but which are also useful in other forms of assays including, but not limited to immunoenzymometric assays, competitive assays, and displacement assays.

How these and other aspects of the invention are achieved will be seen upon review of the disclosure which follows.

BRIEF DESCRIPTION OF THE FIGURES

FIG. 3 shows another embodiment of the invention referred to as the "Delayed Physical Application System".

FIG. 4 provides an embodiment of the invention referred to as the "delayed diffusion application system".

DETAILED DESCRIPTION OF PREFERRED EMBODIMENTS

Figure 1:
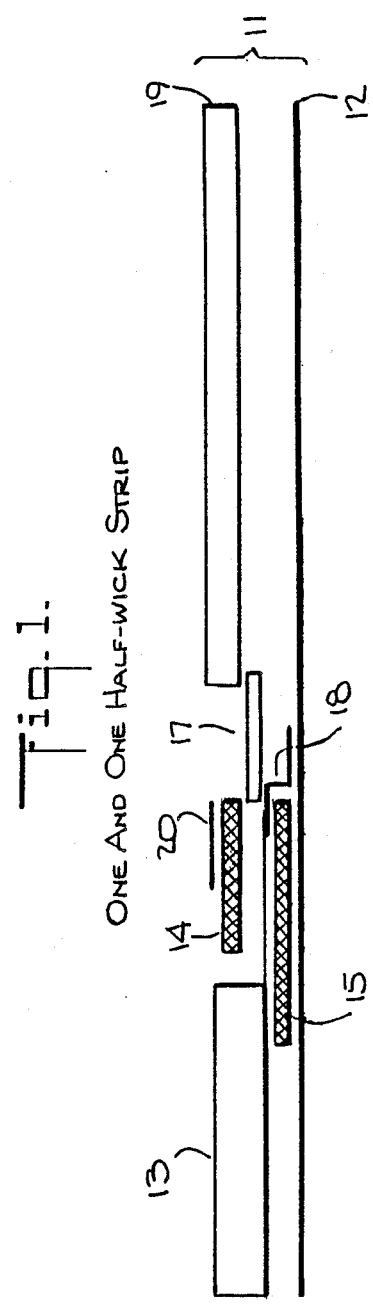
FIG. 1 depicts one embodiment of the invention, referred to as the "1½ wick strip".

Referring now to FIG. 1 a test strip 11 provided by this invention is shown. A stable carrier foil 12 is provided, which gives support to the entire apparatus. Optional sponge 13 is shown, which may contain, e.g., a buffer or other reagents useful in preparing the sample for analysis. Sample may be applied to first zone 14, by, e.g., pipette, and the sponge may be dipped directly into a liquid, or liquid may be applied directly by, e.g., a pipette.

The "first zone" is shown at 14, and contains at least one of the analyte to be determined, an analogue of this analyte, or a non-solid phase bound receptor which binds to the analyte being determined. Various substances are possible. Although it will frequently be the case that the analyte being determined is an antigen, such as a viral protein, a drug or drug residue, and so forth, other substances may be determined, especially if the sample being analyzed is not a biological fluid. The first zone 14 may also contain, in the case of a sandwich assay the two monoclonal antibodies from the same species which bind to the analyte being determined. When a sandwich assay is being performed, one of the two monoclonal antibodies contained in first zone 14 ill carry a label, such as an enzyme.

The "third zone" 15 contains a substrate for the label carried by first zone 14. This substrate can be, e.g., a substrate acted upon by the enzyme, such as a beta galactoside when the enzyme is beta galactosidase. It may be a substance which is necessary for the label to function. For example, the substrate of the third zone may be a substance which combines with the label of the first zone to form a fluorescing moiety, or a functioning molecule. For example, the label and substrate may be halves of a complete enzyme which do not possess catalytic activity until brought together.

The first and third zones must be kept separate from each other, so that premature reaction between label and substrate does not occur. This is achieved via the blocking means 16, positioned between first and third zones 14 and 15. This blocking means need not be made of any particular material, as long as it prevents diffusion between the zones in 14 and 15 until the sample has entered the second zone.

The second zone 17 contains a solid phase bound receptor which binds to any of the reagent in first zone 16 which does not react with analyte from the sample, or when a sandwich assay is being performed, this second zone contains a solid phase bound receptor which binds only to the Fc portion of a monoclonal antibody.

An alternate construction divides this second zone into two portions, one of which is Fc specific, and the other which is not. In this case, formation of a signal, of course, is related to whether the quarternary complex formed, or did not. The non-specific matrix bound antibody thus serves as a negative control.

It is to be noted that the first zone 16 and second zone 17 must be in at least partial fluid contact with each other. Second zone 17 and third zone 15 may be in fluid contact, but need not be. The embodiment in FIG. 1 actually shows no fluid contact between the second and third zones, because of the presence of barrier foil 18. This barrier foil serves to retard the passage of substrate from the third zone into the second zone. This permits whatever reactions are to occur between the solid phase bound component and the unreacted reagent of the first zone or sandwiches of mAb—Ag—Fab* to occur without premature formation of signal. As the substrate must, eventually enter the second zone, barrier 18 is made of fluid permeable material, preferably a polyvinyl alcohol, or material which, via contact with a surfactant or surface active agent, is made fluid permeable.

Fourth zone 19 is in contact with second zone 17, and receives excess sample and reagents therefrom. It acts as a "waste receptacle" for the device as a whole.

An optional cover slip 20 is provided as well. This gives additional stability to the device.

Figure 2:
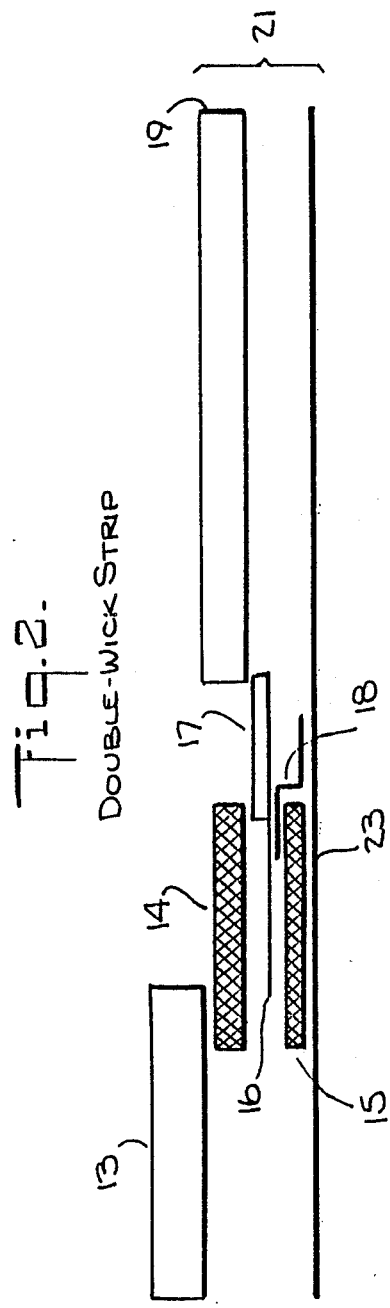
FIG. 2 shows another embodiment of the invention, referred to as the "double wick strip".

In FIG. 2 a modification of the device of FIG. 1 is shown. In device 21, all components are the same as in device 11, except it will be noted that sponge 13 now contacts first zone 14 directly, and does not contact third zone 15 directly. Rather, there is partial fluid contact between the first and third zones. Premature contact of label and substrate is avoided by positioning these at, e.g., the thatched positions 22 and 23, which are separated from each other by barrier 16.

FIG. 3 shows an embodiment where the optional sponge 13 of FIGS. 1 and 2 is not used. Here, the device 31 contains first zone 32, to which sample is added directly. First zone 32 functions as does first zone 14 in FIGS. 1 and 2. It is in partial fluid contact with second zone 33, which, of course, functions in the same way as does the second zone 17 of FIGS. 1 and 2. A key distinction between the device of FIG. 3 and that of FIGS. 1 and 2 is the placement and construction of the third zone, which contains the substrate. As will be seen by reference to FIG. 3, the third zone, containing portions 34 and 35, is below the second zone and is in fluid contact therewith. The third zone contains substrate in region 35, and is supported by layer 34.

When layer 34 receives fluid which has migrated through component 43, it brings substrate 35 into contact with the second zone. Blocking layer 44 prevents fluid contact between zone 1 and component 43. Component 34 may be, for instance, a compressed sponge which swells when contacted by fluid.

In this configuration, premature reaction of label and substrate is not an issue, because by the time fluid reaches the third zone and releases the substrate, any reaction between the labeled reactant of the first zone and the solid phase bound reactant of the third zone has already taken place. The substrate diffuses into the second zone, where the detectable moiety is formed. Excess sample and reagents are carried into fourth zone 19, as in the embodiment of FIG. 1, and the whole device is again held together by carrier foil 12.

An optional feature presented by this device is the covering means 36. The covering means allows for more precise observation of the reaction going on in the test strip. Generally, this covering means permits only selective viewing by providing viewing means or "windows" at various positions. Only one viewing means is actually necessary, and this should be over the second zone 33, so that formation of detectable moiety can be observed there. If the covering means 36 contains additional viewing means over fourth zone 19 one can observe reaction between substrate and labeled binding partner, e.g., or unreacted labeled Fab fragment. Also, if covering means 36 is adapted for use in, e.g., the device or FIGS. 1 and 2, a viewing means can be provided at a point where zones 1 and 3 meet. This allows the investigator to determine if premature mixing of label and substrate has occurred. The covering means can be made of various materials, including foils. It can also be an injection molded lid or cover which is part of an injection molded case or container means.

FIG. 4 differs from the device of FIG. 3, in that protective layer 37 covers substrate 35 in the third zone, and substrate diffusion into zone 2 is initiated by fluid from zone 2 penetrating protective layer 37. This gives greater assurance that premature mixing of substrate will not take place. The covering means 36, which, it has been pointed out, is optional, is not included in this embodiment, although it could have been.

Figure 5:
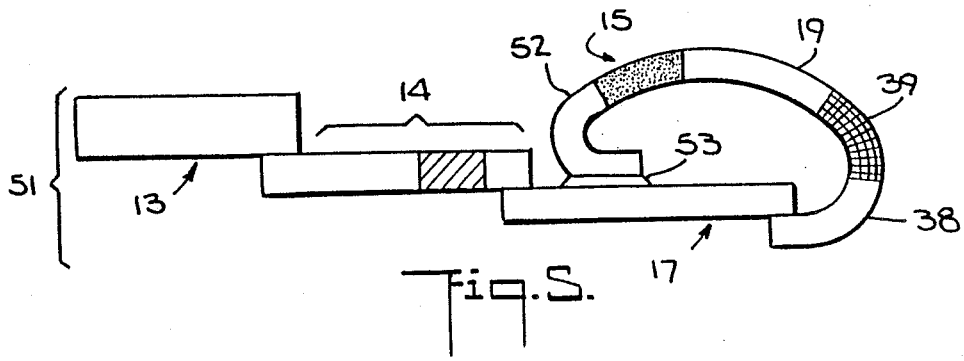
FIG. 5 is an embodiment known as the "loop strip".

FIG. 5, the "loop embodiment" depicts the embodiment of the device where sponge 13 is used for sample application, as in FIG. 2, supra. The sample passes into the first zone 14, where the reaction between, e.g., analyte and binding partner or mAb, Fab*, and Ag takes place. The whole content of first zone 14 passes to second zone 17, where either unreacted labeled substance or sandwiches are picked up by the solid phase bound reactant situated here. Anything not bound in second zone 17 is carried via means 38 through 39, which retains any label. The excess portion of the fluid sample enters waste 19 but, rather than being held here, the configuration of the device is such that the sample is forced into third zone 15, which contains the label substrate. As the configuration forces passage into third zone 15, it also precludes passage back to 19. Via means 52, the substrate containing material now passes through barrier 53 back into second zone 17, where reaction of solid phase bound labeled reactant and substrate takes place. Barrier 53 is selected so that while sample can pass through it from means 52, it cannot pass up from second zone 17.

Figure 6:
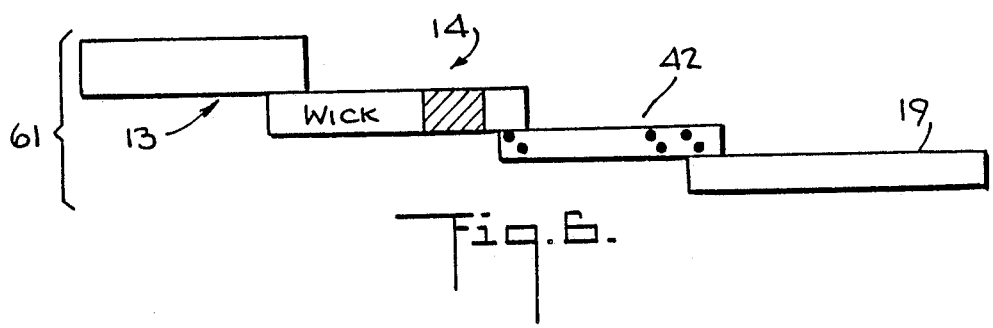
FIG. 6 shows an embodiment of the invention called the "Integral Matrix Strip".

FIG. 6 shows the "integral matrix" embodiment of the device. In this embodiment, the second and third zones essentially become one in matrix 42. The substrate is incorporated into this matrix by means which may include, but are not limited to, encapsulation. The combining of the two zones in one matrix requires that the substrate not be released until such time as the labeled reactant from first zone 14 has reacted with solid phase bound material contained herein.

Figure 7:
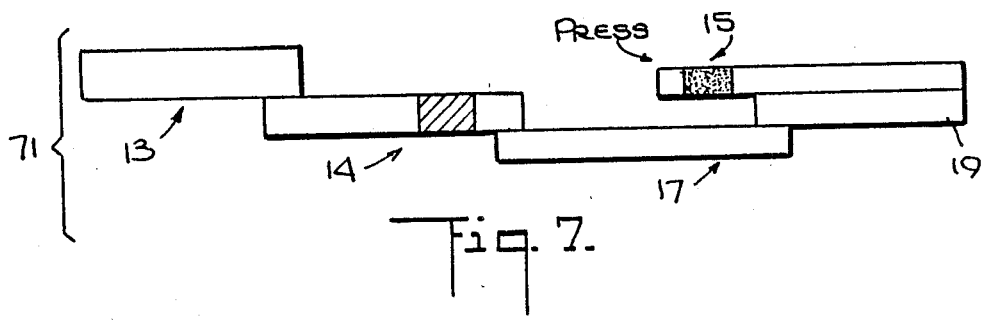
FIG. 7, shows a model of the invention known as the "external pressure strip".

The final pictured embodiment in FIG. 7 shows device 71. Here, all of the depicted elements are as in FIGS. 1 and 2, except that in this embodiment the third zone containing the substrate 15 is separated from second zone 17. Only by applying an external force to 15 can be substrate be brought into contact with the solid phase bound label.

Various assays may be performed in any and all of the preferred embodiments shown in FIGS. 1-7. For purposes of illustration, the mechanics of a different assay using the device of FIGS. 1, 4, and 5 are set out, although it will be clear to the skilled artisan that any and all of these may be adapted for use in any of the devices.

In performing a test for the presence of thyroxin (also called T4) in blood, e.g., a sample is applied to first zone 14 of the device of FIG. 1. Tap water is applied to sponge 13 and migrates into third zone 15. The first zone contains T4 specific antibodies carrying the enzyme label horseradish peroxidase, while zone 15 contains any of the standard horseradish peroxidase substrates, such as orthophenylenediamine. The sample begins moving toward second zone 17, which contains, in solid phase bound and immobilized form, either T4 itself or related molecule T3. In moving through zone 14, any T4 in the sample has reacted with the horseradish peroxidase labeled T4 specific antibodies to form complexes. These, together with uncomplexed antibodies wash into second zone 17 ahead of the fluid which traveled through zone 15. The differential diffusion occurs because of the barrier 18.

While barrier 18 is dissolving, any uncomplexed antibody reacts with the solid phase bound T3 or T4 in the second zone 17, and the previously formed T4-antibody complex passes into waste zone 19. Substrate for horseradish peroxidase now passes into second zone 17, where it reacts with the enzyme immobilized on the solid phase. This produces a quantifiable signal, as will be recognized by those skilled in the art. The amount of enzyme caught by the solid phase is a measure of how much Tor T4 was in the sample.

Similarly, one may perform a sandwich assay for, e.g., carcinoembryonic antigen (CEA), a multiepitopic substance, using the device of FIG. 4. In such a test, first zone 32 contains both mouse-anti-human CEA monoclonal antibodies, and mouse-anti-human CEA monoclonal antibody Fab fragments labeled with beta galactosidase. Upon contact of first zone 32 with the sample, a sandwich forms between the whole antibody (MAb), the CEA (Ag) and the fragment (Fab*). This mAb—Ag—Fab* sandwich, together with unreacted mAb and Fab* pass into second zone 33, which contains, bound and immobilized to a solid phase, a sheep-antimouse Fc specific antibody. This solid phase binds both the sandwich described supra, as well as any excess mAb. As Fab* contains no Fc portion, however, this is not bound, and passes into the waste zone. Meanwhile, some of the sample has released the substrate resorufin beta galactopyranoside, which moves into the second zone 33. This substrate reacts with the Fab* fragments bound in this region, giving an indication of the presence and amount of CEA in the sample.

Using the device of FIG. 5, one can perform a competitive assay for determining if a subject has been exposed to the HIV virus. This type of test assays for antibody rather than antigen, so it shows that, for purposes of this invention, these are equivalent.

Antibody to gp120 of HIV which is conjugated to an enzyme, such as a peroxidase, is incorporated into first zone 14 of device 51. A serum sample which may contain antibodies to HIV is introduced at sponge 13, and diffuses into 14. The mixture of sample and conjugate passes into second zone 17, which contains, immobilized in solid phase, HIV gp120 sufficient to bind all of the labeled IgG if there is no other antibody present. Unbound conjugate will pass via means 38 into trap 39, which removes any free label from the sample. The remaining solution passes through third zone 15, releasing substrate, which passes via one way barrier into the matrix, where it reacts with bound label. There is an indirect correlation—i.e., the more label which bound, the less antibody there was in the sample, and vice versa.

Different materials may be used in each facet of the invention. As receptors, while antibodies are preferred, additional materials such as protein A, and biotin-avidin complexes, among others, can be used.

The immobilized receptor which forms the fourth part of the quaternary complex may be any of the materials listed supra, as long as it binds the first monoclonal antibody and does not bind monoclonal antibody fragments. Especially preferred are antibodies which bind to the Fc portion of other antibodies, but do not bind fragments.

When an antibody is used as the solid phase, a monoclonal antibody is preferred, although polyclonal antisera can also be used. The species in which the solid phase bound antibodies is generated is not important as long as there is no cross reactivity between the first receptor and the monoclonal antibody Fab fragment. The monoclonal antibody which binds to the antigen and the monoclonal antibody Fab fragment do derive from the same species, however.

The label used on the Fab fragment may be any of the conventional labels used in immunoassays, but especially preferred are enzymes which react with their substrates to form colored substrates. Examples of such enzymes are beta galactosidase, horseradish peroxidase, alkaline phosphatase urease and amylase, although it will be recognized that these are only examples and are not to be read as limits on what enzymes can be used. It will be clear to the skilled artisan, that when avidin is the matrix bound receptor, a biotinylated monoclonal antibody can be used. When this is the case, the labeled component need not be a Fab fragment, but can be a whole mAb.

The positioning of the labeled Fab fragment or mAb and first unlabeled or biotin/avidin labeled antibody in the first zone is not a critical feature of the invention. These can be positioned so that the sample reaches one before the other, or so that there is simultaneous contact.

The material of which the device is constructed can include many different items. Of course, the various zones must be absorptive of liquids and possess good capillarity. Examples of such materials are bibulous paper, nitrocellulose paper, sponges, and other absorptive materials. These may be fibrous or not, and the different zones can be composed of different materials possessing different degrees of capillarity, absorption, and so forth.

The receptor is immobilized via any of the standard known means in the art for immobilizing such receptors, e.g., to a solid support, such as by fixing with cyanogen bromide.

As mentioned supra, when the barriers are used in the apparatus, they must be chosen so that they permit fluid passage. Inert polymers are preferred, and especially preferred is polyvinyl alcohol (PVA). Other suitable materials will be evident to the skilled artisan.

When the cover means is used, its openings must be open, transparent or translucent. One preferred material for this is transparent mylar, while the rest of the cover can comprise suitably sturdy material, such as metallic foil may or may not be covered with a transparent material.

The additional features of the invention, such as the support and the impermeable barrier between the first zone and the substrate zone comprise conventional materials known to the art.

The following example illustrates the operation of the invention, but is not to be read as any limitative of the preceding discussion.

EXAMPLE

An apparatus for determining human chorionic gonadotropin (hCG) was prepared and tested.

A piece of 4210 paper (Firma Kalff) was cut into a strip 2.6 cm long and 0.6 cm wide (first zone). One end was impregnated with 10 $\mu$l PBS buffer (pH 7.0, 1% BSA, 0.1% Tween 20), and its center portion was impregnated with 7.5 $\mu$l of a solution containing 20 U/ml of a conjugate of an Fab portion of a monoclonal antibody against hCG and beta galactosidase. The monoclonal antibody fragment had no cross reactivity against luteinizing hormone. This portion was also impregnated with 75 $\mu$l of a 100 $\mu$g/ml solution of a monoclonal antibody against the beta chain of hCG. The end of the strip opposite the buffer impregnated end was impregnated with 10 $\mu$l of an aqueous solution of 5% polyvinyl alcohol. The resulting strip overlapped 0.5 mm of a strip of 3512 paper from Schleicher & Schull (second zone) which was 1 cm long and 0.6 cm wide. This paper had been activated using cyanogen bromide, and a sheep antibody against the Fc portion of mouse antibodies was fixed thereto. This strip overlapped 0.5 mm of a 5 cm long and 0.6 cm wide strip of D28 paper (Whatman), impregnated with 150 $\mu$l of an aqueous solution of 18% polyvinyl alcohol (waste zone). The three strips, overlapped as indicated to form a continuous strip, were mounted on a 10 cm long, 0.6 cm wide strip of polystyrene using adhesive tape. The strips thus produced were dipped, one each, into urine samples calibrated as containing 0, 100, 250, and 500 mIU/ml hCG. After 5 minutes, each strip was dipped into a solution of 0.8 mmol resorufin beta-galactopyranoside in 100 mmol Hepes buffer (pH 7.5), and allowed to develop for 5 minutes. All strips dipped into hCG containing urine exhibited bright fuchsia color at the second and waste zones, while the strip dipped in the sample containing no hCG as yellow in the second zone and fuschia in the third zone. The change in color is indicative of the action of beta galactosidase on the resorufin beta galactopyranoside in the second zone and waste zone.

The foregoing example, it will be seen, could be modified very easily by, e.g., having the resorufin beta galactopyranoside impregnated into a separate zone in the manner described supra, and the development of the color change could be observed through a covering means as has also already been described.

While there have been described what are at present considered to be the preferred embodiments of this invention, it will be obvious to one skilled in the art that various changes and modifications may be made therein without departing from the invention, and it is, therefore, aimed to cover all such changes and modifications as fall within the true spirit and scope of the invention.

We claim:

1. Method for determining a component of a liquid sample comprising contacting said sample with a solid support, said support having incorporated therein a removable first monoclonal antibody which binds to said component and a labeled monoclonal antibody or fragment of a monoclonal antibody which binds to said component wherein said first monoclonal antibody and said labeled monoclonal antibody or monoclonal antibody fragment are derived from the same species under conditions favoring formation of a complex of said first monoclonal antibody said component and said labeled monoclonal antibody or fragment, contacting said complex with an immobilized second receptor which binds to said first monoclonal antibody but not to said labeled monoclonal antibody or fragment under conditions favoring formation of a quaternary complex between said first complex and said immobilized receptor, and measuring label either in said quaternary complex or in a residue of said sample as a measure of said component.

2. Method of claim 1, wherein said second receptor is an antibody specific for the Fc portion of said first monoclonal antibody.

3. Method of claim 1, wherein said second receptor is an antibody and said fragment is a Fab fragment.

4. Method of claim 1, wherein said sample is contacted with said monoclonal antibody fragment and said monoclonal antibody simultaneously.

5. Method of claim 1, wherein said sample is contacted in sequence with said first monoclonal antibody and said labeled monoclonal antibody or monoclonal antibody fragment.

6. Method of claim 1, wherein said monoclonal antibody fragment label is an enzyme.

7. Method of claim 1, wherein said monoclonal antibody fragment label is radioactive.

8. Method of claim 1, wherein said monoclonal antibody fragment label is fluorescent.

9. Method of claim 1, wherein said enzyme is beta galactosidase.

10. Method of claim 1, wherein said measuring comprises contacting said quaternary complex with a color forming substrate for said label and measuring color thus formed as a measure of said component.

11. Method of claim 1, wherein said first monoclonal antibody carries a member of a biotin avidin complex and said immobilized second receptor is a binding partner of said complex.

* * * * *